(12) United States Patent
Sogaro

(10) Patent No.: US 6,447,476 B1
(45) Date of Patent: Sep. 10, 2002

(54) PREFILLED TELESCOPING AMPOULE DEVICE

(75) Inventor: Alberto Sogaro, Kronberg (DE)

(73) Assignee: Dentaco Dentalindustrie-und Marketing GmbH, Bad Homburg (DE)

( * ) Notice: Subject to any disclaimer, the term of this patent is extended or adjusted under 35 U.S.C. 154(b) by 0 days.

(21) Appl. No.: 09/443,512

(22) Filed: Nov. 19, 1999

(51) Int. Cl.$^7$ .............................................. A61M 37/00
(52) U.S. Cl. ..................................................... 604/85
(58) Field of Search ........................ 206/221; 604/183, 604/85, 212, 213, 218, 223, 232; 401/123

(56) References Cited

U.S. PATENT DOCUMENTS

| | | | |
|---|---|---|---|
| 2,478,844 A | 8/1949 | Smith ........................... | 128/215 |
| 4,391,590 A | 7/1983 | Dougherty .................... | 433/90 |
| 4,741,737 A | 5/1988 | Meyer et al. ................. | 604/140 |
| 4,793,476 A | 12/1988 | Schrupp ....................... | 206/222 |
| 4,809,711 A | 3/1989 | Meyer et al. ................. | 128/766 |
| 5,330,048 A | 7/1994 | Haber et al. ................. | 206/221 |
| 5,636,931 A | 6/1997 | Gueret ......................... | 401/126 |

FOREIGN PATENT DOCUMENTS

| | | | | |
|---|---|---|---|---|
| CH | 367284 | 3/1963 | | |
| DE | G 92 02 654.0 | 6/1992 | ........... | A61C/13/12 |
| DE | 4406503 A1 | 8/1995 | ........... | A61C/13/12 |
| EP | 0 090 413 | 10/1983 | ........... | B65D/83/00 |
| EP | 0 295 265 B1 | 3/1987 | ........... | A61C/13/12 |
| EP | 0 332 487 A1 | 2/1989 | ........... | A61C/13/12 |
| EP | 0 577 200 A1 | 6/1993 | ........... | A61C/13/12 |
| EP | 0 688 516 A1 | 5/1995 | ........... | A61C/13/12 |
| FR | 2182522 | 12/1973 | ........... | A61C/13/12 |
| WO | 92/08506 | 5/1992 | | |

OTHER PUBLICATIONS

USSN 09/171,446 filed Aug. 19, 1999, Multi–Chamber Ampoule for Measuring Doses of Liquids, Alberto Sogaro.

PCT Search Report from Appln. No. PCT/DE98/00430, dated Aug. 4, 1998.

Patent Abstract of Japan, Publ. No. 08187121, Publ. dated Jul. 23, 1996, "Applicator for Liquid Material Having Adhesion," Yaita Shigeru.

*Primary Examiner*—Brian L. Casler
*Assistant Examiner*—Kevin C. Sirmons
(74) *Attorney, Agent, or Firm*—Quarles & Brady LLP

(57) ABSTRACT

An improved prefilled, telescoping ampoule device having a simplified construction allows for passage of fluid from one component to the other without leakage. The telescoping ampoule device can be manufactured and assembled in an efficient manner and provides for adaptation to various application purposes without a change of basic design.

38 Claims, 6 Drawing Sheets

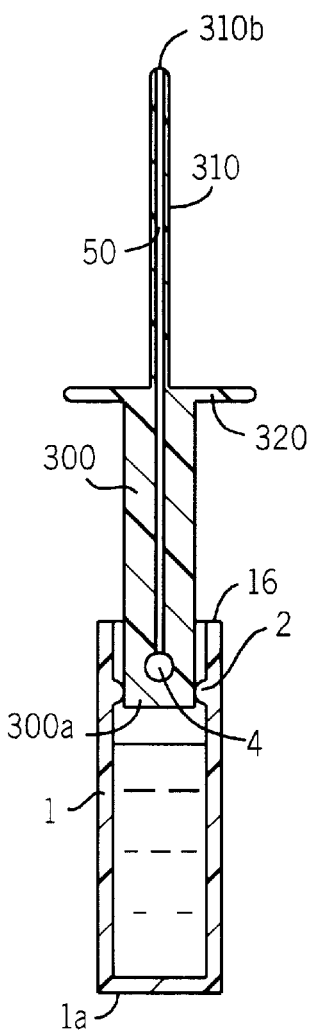 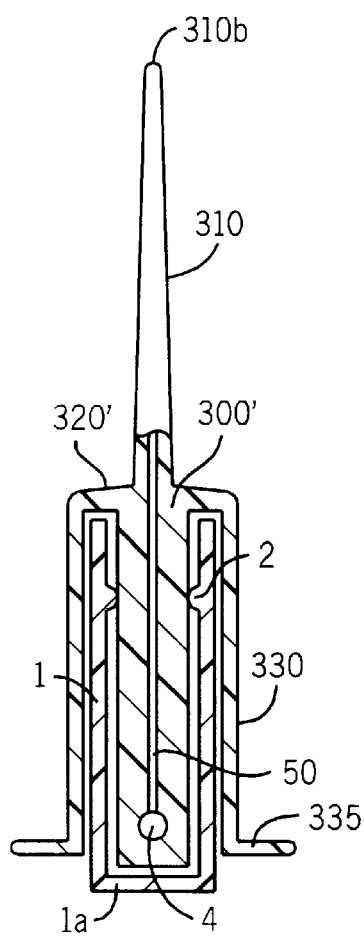 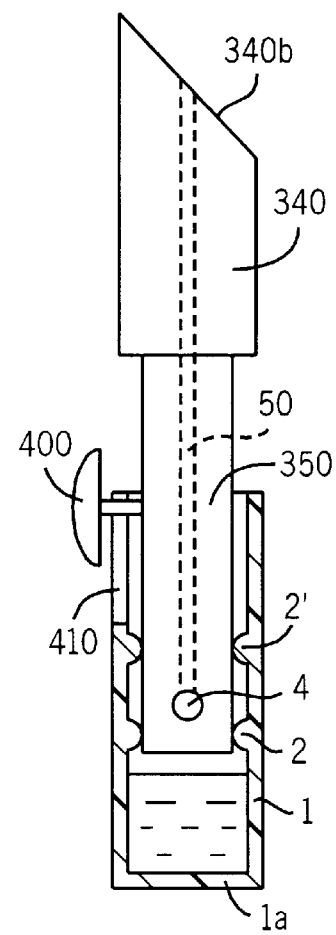
FIG. 10　　　　FIG. 11　　　　FIG. 12
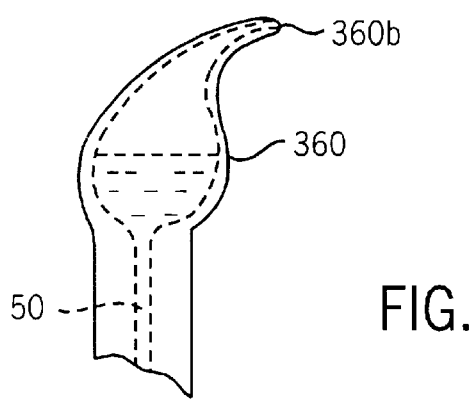
FIG. 13

PREFILLED TELESCOPING AMPOULE DEVICE

BACKGROUND OF THE INVENTION

Safe and hygienic application of predetermined doses of medical fluids such as eye drops and the like rely on an adequate storage of those doses in an ampoule device without danger of introducing contaminants. Substantially, the same holds true for cosmetic samples in form of predetermined amounts of a cosmetic fluid prefilled in an ampoule device for a single use by test persons without danger of contamination through use of other persons.

Usually, those non-refillable ampoule devices should have a construction being as simple as possible, cheap in production and, furthermore, offering, despite of their simple construction, a reliable performance and easy manipulability for the patient or customer, respectively.

These features should also be maintained as far as possible for prefilled ampoule devices in which two or more fluids have to be stored in such a way that it is possible to apply the mixed fluid components.

For the above purposes, there have been developed a plurality of ampoule or vial devices with one or a plurality of chambers offering the possibility of applying a desired amount of fluid by means of a brush or other tool to be inserted into the chamber or chambers, respectively, or alternatively, by means of a syringe or nozzle-like mechanism combined with the vial or ampoule device. (U.S. Pat. No. 5,636,931, Patent Abstracts of Japan vol. 096, no. 011, 29. November 1996 & JP 08 187121 A, EP 0577200A1, U.S. Pat. No. 3,870,147, DE 9202654, U.S. Pat. No. 4,927,282, U.S. Pat. No. 4,793,476, EP 0 295 265 B1, WO 9208506, U.S. Pat. No. 5,330,048, EP 0090413 A1, U.S. Pat. No. 2,478,844, CH 367284, DE 4406503, U.S. Pat. No. 4,391,590).

Before applying the fluid or fluid mixture, the user must operate a mechanism for providing access to the fluid or fluid mixture. A plurality of solutions require rupturing a closure member or a weakened breaking point. Other solutions merely require a telescopic action between at least two device members in order to transfer the application fluid into an accessible chamber. Such a solution is e.g. disclosed in U.S. Pat. No. 4,741,737 and U.S. Pat. No. 4,809,711 of Meyer et al describing a prefilled ampoule-syringe.

Furthermore, the inventor of the present application disclosed in his earlier WO 98/63994 (U.S. Pat. No. 6,227,736 filed on Oct. 20, 1998), assigned to the same assignee as the present application, a prefilled ampoule device with a brush-like application tool, having an outer sleeve and an inner sleeve being subjected to a telescoping movement. The inner sleeve is liquid-tightly and slidingly provided in the outer sleeve, and it has transverse openings near its bottom. Above the openings, the inner sleeve comprises an annular sealing groove which, in the closed storage position of the ampoule device, engages an annular sealing lip protruding from the inner wall of the outer sleeve. In addition to the sealing means, locking means are provided for locking the inner sleeve within the outer sleeve.

Though a plurality of devices have already been developed especially for medical purposes there is still a need for a simplified construction which, nevertheless, is reliable and easy to manipulate.

SUMMARY OF THE INVENTION

The main object of the present invention is to provide an improved prefilled ampoule device which has a simplified construction, can be manufactured and assembled in an easier manner and at less expense, and offers the possibilty of adapting it to various application purposes without changing the basic design.

This main object is achieved in a prefilled telescoping ampoule device comprising:

- a receptacle made of elastomeric material including a hollow cylindrical body having a closed lower end, an open upper end, and a peripheral sealing lip projecting radially inwardly from the inner wall of the cylindrical body between the closed lower end and the open upper end thereof;
- an insertion member including a cylindrical portion having a closed lower end, an open upper end, a transverse opening radially extending from the outer wall into the interior of the cylindrical portion, and a longitudinal passage axially extending within the interior of the cylindrical portion from the transverse opening to the open upper end of the cylindrical portion;
- the cylindrical portion of the insertion member with its closed lower end ahead being inserted into the open upper end of the hollow cylindrical body and being arranged therein for coaxially telescoping movement of the receptacle and the insertion member towards one another from a closed storage position to an open release position;
- wherein, in the closed storage position, the closed lower end of the cylindrical portion of the insertion member is spaced a distance from the lower end of the hollow cylindrical body so as to define therein a cylindrical chamber containing a substance, and the peripheral sealing lip of the cylindrical body is sealingly pressed into circumferential contact with the outer wall of the cylindrical portion of the insertion member at a location above the closed lower end of the cylindrical body and below the transverse opening so as to prevent release of substance from the chamber into the transverse opening and to frictionally hold the insertion member in place within the receptacle during transportation and storage, and
- wherein in the open release position, after telescoping movement the lower end of the cylindrical portion of the insertion member is positioned at or close to the lower end of the cylindrical body of the receptacle and the transverse opening of the cylindrical portion of the insertion member is located below the sealing lip of the cylindrical body resulting in a reduced volume of the chamber and a release of substance from the chamber into the transverse opening and the longitudinal passage of the cylindrical portion of the insertion member, and the sealing lip of the cylindrical body is sealingly pressed into circumferential contact with the outer wall the cylindrical portion of the insertion member at a location above the transverse opening so as to prevent escape of substance from the chamber to the upper open end of the hollow cylindrical body of the receptacle.

A main advantage of the present invention is that it achieves a reliable performance by providing a single sealing lip without a corresponding sealing groove and any additional locking means.

The prefilled substance is accessible by dipping an applicator tool such as a brush into the insertion member in the open release position of the device or, alternatively, is ejected from the open end of insertion member during the telescoping movement from the closed storage position to the open release position.

In adapting the device of the present invention to the first alternative the longitudinal passage of the cylindrical portion of the insertion member has in relation to the outer diameter of the cylindrical portion a large inner diameter so as to define a cylindrical chamber within the cylindrical portion of the insertion member.

In adapting the device to the second alternative the insertion member includes a coaxially extending tubular portion integrally formed on top of the cylindrical portion having a smaller outer diameter than the cylindrical portion and ending on its upper end in an open tip, and the longitudinal passage is provided in form of a narrow conduit extending from the cylindrical body into the tubular portion up to the open tip thereof.

Furthermore, due to the simple construction, it is possible to provide more than one insertion member such that after telescoping movement of all insertion members and the outermost receptacle two or even more prefilled substances are mixed with each other. Hence, it is possible to mix several prefilled liquid substances or even a prefilled solid substance with liquid substances.

Whenever a second or even a third substance is provided within a first or even a second insertion member an additional sealing lip is provided in the receptacle such that, in the closed storage position, this additional sealing lip is provided above the transverse opening of the only or first insertion member. This additional sealing lip is provided in addition to the sealing lip of the receptacle provided, in the closed storage position, below the transverse opening of the first insertion member and above the closed lower end of the cylindrical portion of the first insertion member. Likewise, whenever a third substance is provided in a second insertion member, two sealing lips are provided on the inner wall of the first insertion member such that, in the closed storage position, one sealing lip is provided below the transverse opening of the second insertion member and above the closed lower end of the cylindrical portion of the second insertion member and an additional sealing lip is provided above the transverse opening of the second insertion member. In this way, it is possible to prevent escape of a first, second or third substance via the transverse openings and through any radial space between receptacle and first insertion member and between first insertion member and second insertion member and so on.

A further aspect of the present invention is the provision of a separate manipulating member including a tubular front portion enclosing an outlet passage and a rear portion integrally formed therewith and enclosing at least one axially extending inlet passage for receiving the tubular portion on top of the cylindrical portion of an insertion member and being in fluid communication with the outlet passage, and the manipulating member including a shoulder transversely extending outwards with respect to the at least one axially extending inlet passage for manually performing telescoping movement between the receptacle and the insertion member.

Another further aspect of the invention is the provision of another separate manipulating member designed for receiving the receptacle and insertion member in the closed storage position and having a retractable slider for manually performing telescoping movement between the receptacle and the insertion member.

BRIEF DESCRIPTION OF THE DRAWINGS

FIG. 10 is a longitudinal sectional view of a fourth preferred embodiment of a prefilled telescoping ampoule device of the present invention with a nozzle-like insertion member having a narrow longitudinal passage, showing the device in its closed storage position;

FIG. 11 is a similar view showing a modification of the device of FIG. 10 in its open release position;

FIG. 12 is a longitudinal sectional view of a modification of the fourth embodiment of the present invention with an insertion member having a narrow longitudinal passage, a slider provided on the outer cylindrical wall of the insertion member and a particular applicator portion provided at the upper end of the insertion member, showing the device in its closed storage position;

FIG. 13 is a longitudinal sectional view showing a modification of the applicator portion provided at the upper end of the insertion member of the device shown in FIG. 12;

DESCRIPTION OF THE PREFERRED EMBODIMENTS

Figure 1:
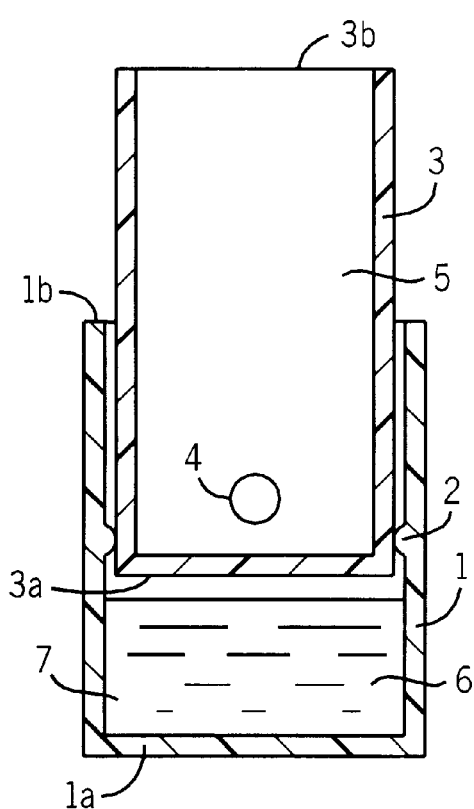
FIG. 1 is a longitudinal sectional view of a first preferred embodiment of a prefilled telescoping ampoule device of the present invention showing the device in its closed storage position.
Figure 2:
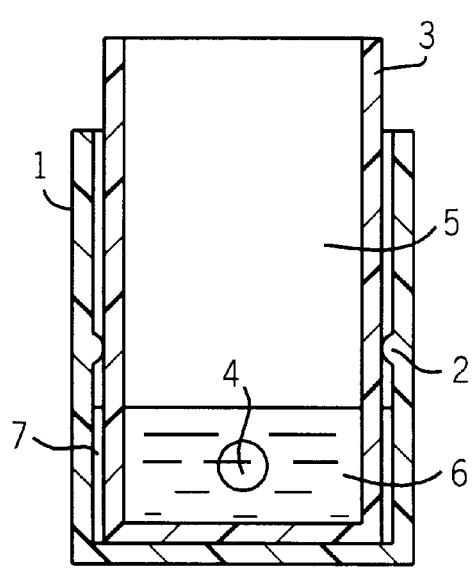
FIG. 2 is a similar view showing the device of FIG. 1 in its open release position.

FIGS. 1 and 2 show a first preferred embodiment of a prefilled telescoping ampoule device of the present invention comprising a receptacle 1, an insertion member 3, and a liquid substance 6.

The receptacle 1 consists of a hollow cylindrical body having a closed lower end 1a, an open upper end 1b axially spaced therefrom, and an annular peripheral sealing lip 2 projecting radially inwardly from the inner wall of the cylindrical body between the closed lower end 1a and the open upper end 1b. The insertion member 3 includes a cylindrical portion having a closed lower end 3a, an open upper end 3b axially spaced therefrom, a transverse opening 4 radially extending, at or near the closed lower end 3a, from the outer wall of the insertion member 3 into the interior of the cylindrical portion, and a longitudinal passage 5 axially extending within the interior of the cylindrical portion from the transverse opening 4 to the open upper end 3b of the cylindrical portion. Accordingly, the longitudinal passage 5 communicates with the transverse opening 4 and, as it can be seen from FIG. 1 and 2, has, in this particular embodiment, a wide lumen (inner diameter) with respect to the outer diameter of the cylindrical portion.

The cylindrical portion of the insertion member 3, after being inserted with its closed lower end 3a ahead into the open upper end 1b of the hollow cylindrical body of receptacle 1, is arranged in the hollow cylindrical body for coaxially telescoping movement of the receptacle 1 and the insertion member 3 towards one another from a closed storage position shown in FIG. 1 to an open release position shown in FIG. 2. In the closed storage position, the closed lower end 3a of the cylindrical portion of the insertion member 3 is spaced a distance from the lower end 1a of the hollow cylindrical body so as to define therein a cylindrical chamber 7 containing the substance 6. In the closed storage position, the peripheral sealing lip 2 of the cylindrical body of the receptacle 1 is sealingly pressed into circumferential contact with the outer wall of the cylindrical portion of the insertion member 3 at a location above the closed lower end 1a of the cylindrical body and below the transverse opening 4. For this reason, during transportation and storage of the device, the insertion member 3 is frictionally held in place within the receptacle 1 and any accidental release of substance 6 from the chamber 7 into the transverse opening 4 and to the open upper end 1b of the receptacle 1 is prevented.

In the open release position shown in FIG. 2, after axial telescoping movement, the lower end 3a of the cylindrical portion of the insertion member 3 is positioned at or near the lower end 1a of the cylindrical body of receptacle 1 and the transverse opening 4 of the cylindrical portion of insertion member 3 is located below the sealing lip 2 of the cylindrical body resulting in a reduced volume of the chamber 7 and a release of substance 6 from the chamber 7 through the transverse opening 4 into the wide diameter longitudinal passage 5 of the cylindrical portion of insertion member 3. In the open release position, the sealing lip 2 of the cylindrical body 1 is sealingly pressed into circumferential contact with the outer wall the cylindrical portion of the insertion member 3 at a location above the transverse opening 4 so as to prevent escape of substance 6 from the chamber 7 to the upper open end 1b of the hollow cylindrical body of receptacle 1 through any space between the outer wall of the cylindrical portion of insertion member 3 and the inner wall of the cylindrical body of receptacle 1 above the sealing lip 2. On the other hand, the substance 6, now essentially fully contained within the hollow cylindrical portion of the insertion member 3, is accessible via the upper open end 3b of the insertion member 3, for example, by manually dipping an applicator means such as a brush into the released substance 6 contained in the cylindrical body of insertion member 3 of the more or less upright held device.

At the start of the axial telescoping movement of the device from the closed storage position to the open release position, a certain axial compression force has to be applied to the axially opposite outer ends of the device in order to overcome an axial counter force internally developed by the device. This axial counterforce essentially consists of the frictional force between the sealing lip 2 and the inner wall of the cylindrical portion of insertion member 3 and a force resulting from any excess pressure within the chamber 7. This latter force prior to any substantial telescoping movement, may increase as a function of the compressibility of the matter sealingly enclosed in chamber 7, such as the liquid substance 6 to be released and air, and also as a function of the characteristics of the materials of the parts 1 and 3 of the device as well as the dimensions of these parts 1 and 3.

In this context, according to the invention, the receptacle 1 is molded from an elastomeric material or any other appropriate material having elastic characteristics, while the insertion member 3 can be molded from a similar material or a relatively rigid plastic material. In a preferred embodiment both parts 1 and 3 of the device are made from polyethylene (PE). Generally, the materials and dimensions, such as the wall thicknesses of both parts 1 and 3 of the device are preferably chosen such that the receptacle 1 in its entirety is more elastic than the insertion member 3. The insertion member can even be rigid, whereas the receptacle 1 should have a certain degree of elasticity to allow both the sealing engagement between the sealing lip 2 and the outer wall of the cylindrical portion of the insertion member 3 and the telescopic movement. With regard to the dimensions of the two parts 1 and 3 in the disassembled state, the outer diameter of the cylindrical portion of the insertion member 3 is larger than the inner diameter of the protruding sealing lip 2 and as large or almost as large as the inner diameter of the cylindrical body of receptacle 1, while in the assembled state the peripheral wall of the cylindrical body of receptacle 1 is slightly expanded radially outwards at and in an axial zone near the sealing lip which is continuously in contact with the cylindrical portion of insertion member 3. Accordingly, the peripheral wall of the cylindrical body of receptacle 1 is radially elastically expanded together with the sealing lip 2 such that the sealing lip 2 is expanded to the outer diameter of the cylindrical portion of insertion member 3. Of course, the overall design is such that during the axial telescoping movement there is adequate radial space or clearance between the inner wall of the cylindrical body of receptacle 1 and the outer wall of the cylindrical portion of insertion member 3 below the sealing lip 2 so that any matter contained in the chamber 7 can flow or can be driven into the transverse opening 4.

Referring to FIGS. 1 and 2, the cylindrical chamber within the cylindrical portion of insertion member 3 extends downwardly beyond the transverse opening 4 so as to provide an additional cup-shaped space between the closed lower end 3a and the transverse opening 4. This cup-shaped space is preferably provided in all embodiments in which the axial length of the transverse opening 4 exceeds or substantially exceeds the relatively small axial width of the annular sealing lip 2. This cup-shaped space ensures that, during the axial telescoping movement when the narrow sealing lip 2 is riding over the transverse opening 4, any liquid substance 6 entering the transverse opening 4 flows down into and gathers in the cup-shaped space, instead of being driven into any radial space between the inner wall of the cylindrical body of receptacle 1 and the outer wall of the cylindrical portion of insertion member 3 above the sealing lip 2.

In this connection it should be noted that a variety of embodiments have been implemented with different degrees of elasticity and different dimensions of both parts 1 and 3. For example, the outer diameter of the device was within a range from several millimeters to several centimeters. Furthermore, the overall design of the device depends on the flowability or viscosity of the liquid or even a solid substance stored in the chamber 7. Hence, a man skilled in the art can imagine that neither part 1 nor part 3 is restricted to a certain diameter, wall thickness, material or elasticity, respectively.

Figure 3:
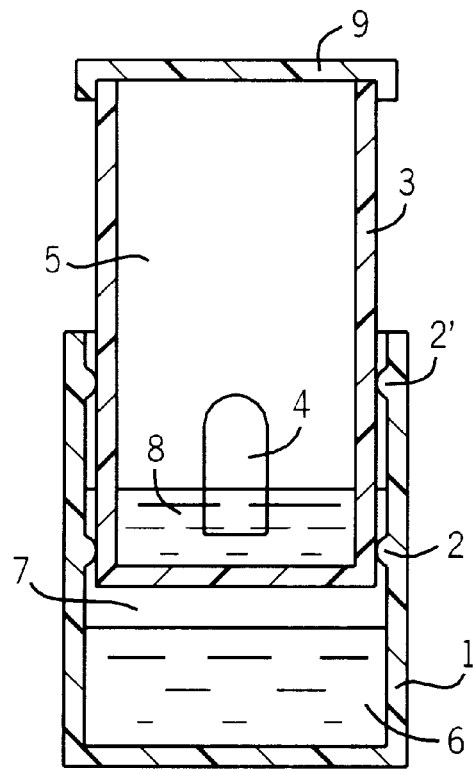
FIG. 3 is a longitudinal sectional view of a second preferred embodiment of a prefilled telescoping ampoule device of the present invention having a cap and storing two separate fluid components, showing the device in its closed storage position.
Figure 4:
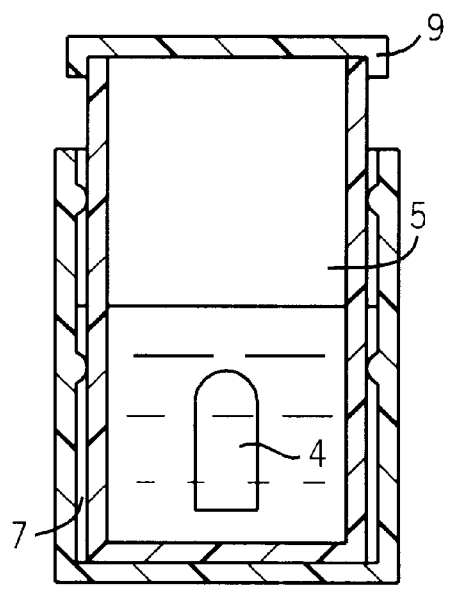
FIG. 4 is a similar view showing the device of FIG. 3 in its open release position.

In the second preferred embodiment shown in FIG. 3 and 4, the hollow cylindrical body of receptacle 1 has an additional annular peripheral sealing lip 2' axially spaced from the sealing lip 2 and projecting radially inwardly from the inner wall of the cylindrical body of receptacle 1. In the closed storage position shown in FIG. 3, the additional annular peripheral sealing lip 2' is sealingly pressed into circumferential contact with the outer wall of the cylindrical portion of insertion member 3 at a location above a longitudinally enlarged transverse opening 4' of the cylindrical portion of insertion member 3 so as to assist in frictionally holding the insertion member 3 in place within the receptacle 1 during transportation and storage. During axial telescoping movement from the closed storage position to the open release position, shown in FIG. 4, the additional sealing lip 2' is sealingly pressed into circumferential sliding contact with the outer wall of the cylindrical portion of insertion member 3 so as to assist in preventing escape of substance from chamber 7 to the upper open end 1b of the hollow cylindrical body of receptacle 1 through any radial space between the inner wall of the cylindrical body of receptacle 1 and the outer wall of the cylindrical portion of insertion member 3 above the lower sealing lip 2. In the closed storage position, additional sealing lip 2' being located above transverse opening 4 also prevents escape of substance through transverse opening 4 and any radial space between the inner wall of the cylindrical body of receptacle 1 and the outer wall of the cylindrical portion of insertion member 3.

In the second embodiment, a second liquid or solid substance 8 to be mixed with the first substance 6 in chamber 7 is contained in the relatively wide diameter longitudinal passage 5 of insertion member 3. The is additional sealing lip 2' assists in preventing escape of substance 8 from the open upper end 1b of receptacle 1 via transverse opening 4' in the closed storage position shown in FIG. 3. A removable cap 9 closing the upper open end 3b of insertion member 3 serves to prevent contamination of the second substance 8 within the hollow cylindrical portion of insertion member 3. The lower sealing lip 2 has the same function as in the first embodiment shown in FIG. 1 and 2. of course, the removable cap 9 or any other similar closure means can also be applied in the first embodiment, especially, if the first embodiment is also used as multi-chamber ampoule device containing a second substance within insertion member 3. It is evident that in this case the first embodiment is dimensioned in a manner that the second substance is prevented from escaping from the upper open end of the cylindrical body of receptacle 1, for example, by fitting the insertion member 3 as tight as possible into the receptacle 1, but still allowing axial telescoping movement from the closed storage position into the open release or mixing position. In this regard, the use of a plug instead of a cap as closure means may be more appropriate as a radial expansion effect can be achieved by the plug.

In both embodiments according to FIGS. 1 to 4, the single substance or the mixed substances, respectively, can be applied by means of an applicator tool (not shown) like a brush which is dipped into the insertion chamber 3 in the open release position of the device. The axial telescoping movement of parts 1 and 3 is manually achieved simply by pressing together both parts with two fingers of one hand.

Figure 5:
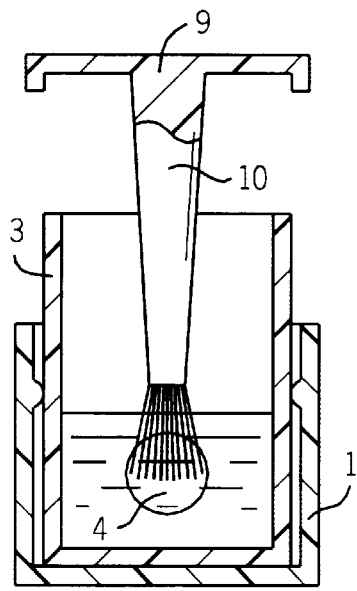
FIG. 5 is a longitudinal sectional view of a modification of the second embodiment of a prefilled telescoping ampoule device of the present invention having a cap holding an applicator tool and showing the device in its open release position.

FIG. 5 shows a modification of the first embodiment in which a brush like applicator tool 10 depends from the inner surface of the cap 9.

Figure 6:
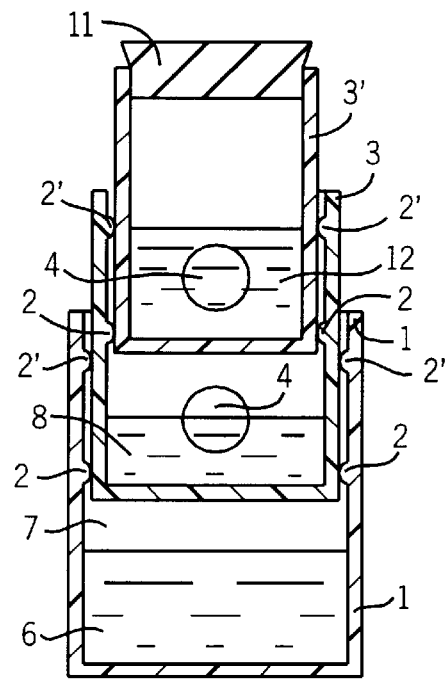
FIG. 6 is a longitudinal sectional view of a prefilled multi-chamber telescoping ampoule device closed by a plug according to a modification of the first embodiment of the present invention, showing the device in its closed storage position.

FIG. 6 shows, in the closed storage position, a further development of the first embodiment including two insertion members 3, 3' and containing three substances 6, 8, 12. The upper innermost insertion member 3' is closed by means of a removable plug 11. The third chamber defined within the cylindrical portion of the upper insertion member 3' contains a third liquid or solid substance 8 which is mixed within the third chamber with the first substance 6 contained in the first chamber 7 of the cylindrical body of receptacle 1 and the second substance contained in the second chamber of the cylindrical portion of lower insertion member 3 when the insertion members 3, 3' and the receptacle 1 are telescopingly moved towards one another from the closed storage position to the open release position (not shown). Likewise, it is principally possible to add even further correspondingly narrower insertion members (not shown) 3", 3'" etc.

It has to be noted that in the multi-chamber embodiment shown in FIG. 6 sealing lip 2 and additional sealing lip 2' are not only provided in the cylindrical body of receptacle 1 below and above transverse opening 4 of the first insertion member 3 in the storage position of the device, respectively. The same principle as already shown in FIG. 3 is also implemented on the inner wall of the cylindrical portion of insertion member 3 which also has a sealing lip 2 and an additional sealing lip 2' being, in the storage position, located above and below the transverse opening 4 of the second insertion member 3'. Hence, as outlined in connection with embodiment shown in FIG. 3 escape of substance through transverse openings 4 and any radial clearance between receptacle 1 and first and second insertion member 3, 3', respectively, is reliably prevented in both positions, the closed storage position and the open release position.

Preferably, the first or lower insertion member 3 is also molded from an elastic material, while the upper or second insertion member 3' can be made from a rigid material. The embodiment shown in FIG. 6 can be further developed by providing a second sealing lip on the inner wall the cylindrical body of receptacle 1, such as lip 2' shown in FIG. 3, and/or an additional sealing lip on the inner wall of insertion member 3.

Figure 7:
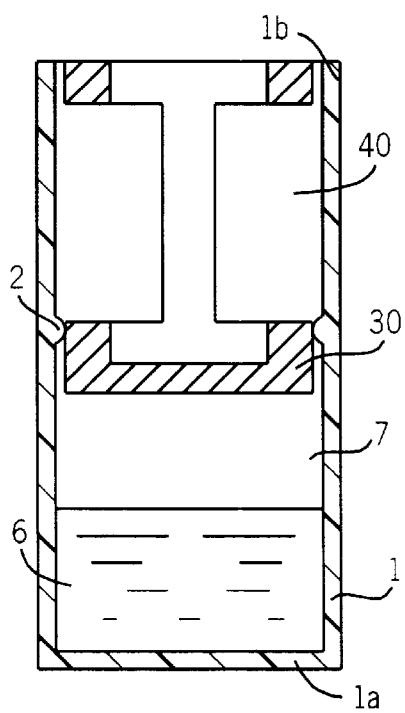
FIG. 7 is a sectional view of a third preferred embodiment of a prefilled telescoping ampoule device of the present invention showing the device in its closed storage position.
Figure 8:
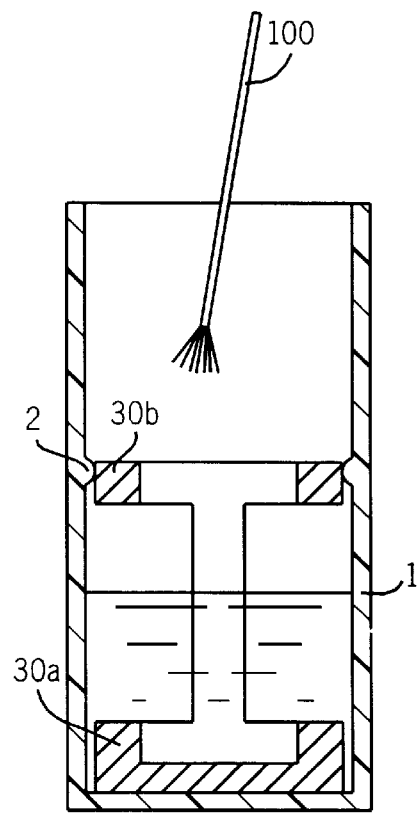
FIG. 8 is a similar view showing the device of FIG. 7 in its open release position together with an applicator tool.
Figure 9:
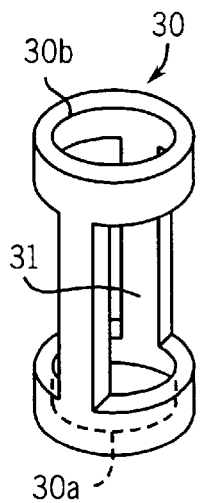
FIG. 9 is a perspective view of the insertion member of the device of FIG. 7 and 8.

The ampoule device shown in FIG. 7, 8 and 9 is a third preferred embodiment which comprises a modified insertion member 30 the open upper end 30a of which, in the closed storage position illustrated in FIG. 7, is flush with the open upper end 1b of the cylindrical portion of receptacle 1. The transverse opening 40 in the outside wall of cylindrical portion of the insertion member substantially extends from the closed lower end 30a to the open upper end 30b of insertion member 30 and circumferentially extends over substantial peripheral portions of the outside wall. In the shown embodiment, the outside wall is reduced to two opposite struts 31 connecting the relatively short cylindrical closed lower end 30a and the rather short ring-shaped open upper end 30b of insertion member 30.

In the closed storage position shown in FIG. 7, the substance 6 within the chamber 7 is sealed off by means of the closed lower end 30a of the insertion member 30 and the sealing lip 2, as explained in connection with the first embodiment shown in FIG. 1 and 2. As the upper ends 1b and 30b of the parts 1 and 30 are flush there is practically no danger of inadvertently displacing the insertion member 30 into the receptacle 1. The open release position shown in FIG. 8 is preferably achieved by inserting a brush-like tool 100 through the open upper end 30b into the insertion member 30 down to the bottom of the cup-shaped closed lower end 30a and then pressing downwards the insertion member 30 by means of tool 100 until the open release position shown in FIG. 8 is reached. In this position the upper end 30b of the insertion member 30 may engage the sealing lip 2 or may be spaced therefrom at a location above the sealing lip 2. Of course, in this embodiment the size of the transverse opening 40 can be reduced to that of the other embodiments or, alternatively cut outs can be provided in the outer wall of the insertion member 30 between the lower end 30a and the upper end 30b.

Furthermore, the upper open end 1b of the receptacle 1 may be provided with a closure means such as a cap in order to store a second substance in the insertion member 30. Preferably, the outer diameter of the open upper end 30b is slightly larger than that of the closed lower end 30a of the insertion member 30.

The ampoule device shown in FIG. 1 presents a fourth preferred embodiment of the present invention comprising a modified insertion member 300 including a coaxially extending tubular portion 310 integrally formed on top of the cylindrical portion having a smaller outer diameter than the cylindrical portion and ending on its upper end in an open tip 310b. The longitudinal passage 50 is provided in form of a narrow conduit extending from the cylindrical body of insertion member 300 into the tubular portion 310 up to the open tip 310b. Preferably, the insertion member 300 includes a manipulating means 320 in form of two projections diametrically radially extending outwards from the cylindrical portion at a location which allows the axial telescoping movement of the receptacle 1 and the insertion member 300 towards one another. In the closed release position (not shown) the projections may abut the upper open end 1b of receptacle 1.

The modified embodiment shown in FIG. 11 differs from the embodiment of FIG. 10 in that the insertion member 300' comprises radial projections 320' which are similar to the projections 320, however, which are integrally connected to two diametrically opposed longitudinal arms 330 extending axially downwards in parallel and in spaced relation to the outer wall of receptacle 1 and ending in a radially outwards extending ring-like portion 335 surrounding receptacle 1. In the open release position shown in FIG. 11, the portion 335 terminates shortly above the closed lower end 1a of receptacle 1.

The tubular release portion 310 of the embodiments of FIGS. 10 and 11 is tapered towards the open upper tip 310b and the longitudinal passage 50 extending up to the open tip is provided in form of a small diameter conduit, achieving a nozzle-like action during telescoping axial movement.

It is, of course, possible to exchange receptacle 1 of FIGS. 10 and 11 by a cascade like system of one receptacle 1 with one or more correspondingly narrower additional cylindrical insertion members 3, 3' as shown in FIG. 6 in order to provide a mixture of two or more substances 6, 8, 12 through tubular release portion 310.

In a modification of the fourth embodiment, shown in FIG. 12 in the closed storage position, the ampoule device comprises an insertion member 350 having a release portion 340 in form of an essentially cylindrical applicator, for example a lip applicator, the outer diameter of which is larger than that of the cylindrical portion of the insertion member 350. The longitudinal passage 50 extends up to the open upper end 340b of release portion 340 and is again designed in form of a small diameter conduit. The open upper end 340b has an essentially plane end face which is inclined with respect to the longitudinal axis of insertion member 350.

FIG. 13 shows a modified release portion 360 replacing release portion 340 in the embodiment of FIG. 12. The release portion 360 is designed in form of a bulgy dropper made of a soft elastomeric material and having an intermediate part of an outer diameter larger than that of the cylindrical portion and ending in an open droplet tip 360b of reduced outer diameter. The longitudinal passage 50 is designed in form of a small diameter conduit in the cylindrical portion and expands to a larger diameter chamber within the intermediate part of the dropper and reduces again to a small diameter outlet in the droplet tip.

In the embodiments of FIGS. 10 to 13, the transverse opening 4 of the cylindrical portion of insertion body 300, 350 has an essentially circular cross section and the sealing lip 2 of the cylindrical body of receptacle 1 has an essentially half-circular cross section of a half-diameter larger than, but in the order of magnitude of that of the transverse opening, particularly, if a second sealing lip 2' is not present. Hence, during telescoping movement, when the lip 2 is riding over the transverse opening 4 the substance 6 can easily flow into the transverse opening 4. Furthermore, the longitudinal passage 50 of these embodiments, apart from that of FIG. 13, has a smaller inner diameter than the transverse opening 4, particularly in the embodiments shown in FIG. 10 and 11 in order to eject the substance from the open upper tip 310b during telescoping movement.

In the ampoule device of FIG. 12 the receptacle 1 has a longitudinal window 410 axially extending from the open upper end 1b of the cylindrical body of receptacle 1 downwards to a location which, in the closed storage position, is above the transverse opening 4 of the cylindrical portion of the insertion member 350. The insertion member 350 has a projection 400 radially extending outwards from the cylindrical portion through the longitudinal window 410 for sliding movement therein during telescoping movement. The outer part of the projection 410 protruding from the longitudinal window may be designed in form of a slider for manual operation.

Figure 14:
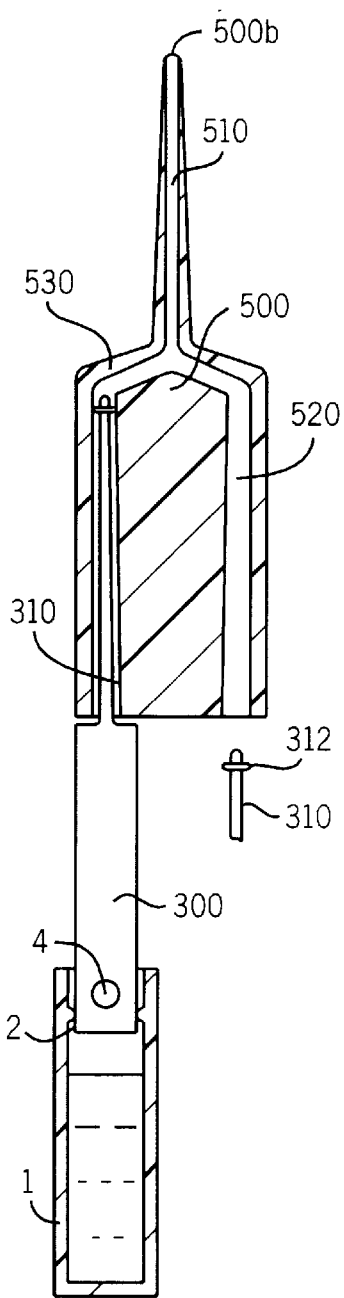
FIG. 14 is a longitudinal sectional view of a further development of the fourth embodiment of the device of FIG. 10 including a separate manipulating member for receiving the tubular portion of the insertion member.

The ampoule device of FIG. 14 substantially corresponds with the device of FIG. 10 and makes use of a separate manipulating member 500 instead of the integrally molded manipulating portion 320. The manipulating member 500 includes a tubular upper portion 500b enclosing an outlet passage 510 and a lower portion integrally formed therewith and enclosing two axially extending inlet passages 520. The inlet passages 520 are designed for receiving the tubular portion 310 on top of the cylindrical portion of an insertion member 300 and are in fluid communication with the outlet passage 510. The manipulating member 500 includes a shoulder 530 transversely extending outwards with respect to the axially extending outlet passage 510 for manually performing telescoping movement between the two receptacles 1 and insertion members 300 when received in the manipulating member 500. This embodiment allows for mixing the substances released from the two insertion members 300 during telescoping movement prior to release from the outlet passage 510. The man skilled in the art will recognize that the manipulating member 500 also may have three or even more integrated axially extending inlet passages 520, or only a single inlet passage 520. Preferably, a sealing lip 312 is provided near the open upper end of the tubular release portion 310.

Figure 16:
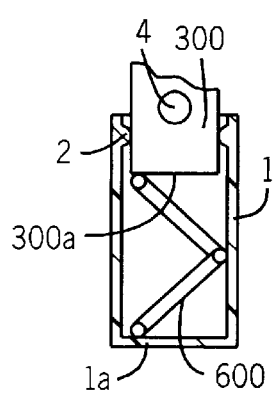
FIG. 16 is a longitudinal sectional view showing a further feature of the embodiments of the present invention.

In each one of the embodiments of the present invention, a spring means 600, shown in FIG. 16, may be provided between the closed lower end 300a of insertion member 300 and the closed lower end 1a of receptacle 1.

In a preferred embodiment, the spring means 600 is integrally formed with the lower end 300a of insertion member 300. This allows a repeated partial release of the substance.

Figure 15:
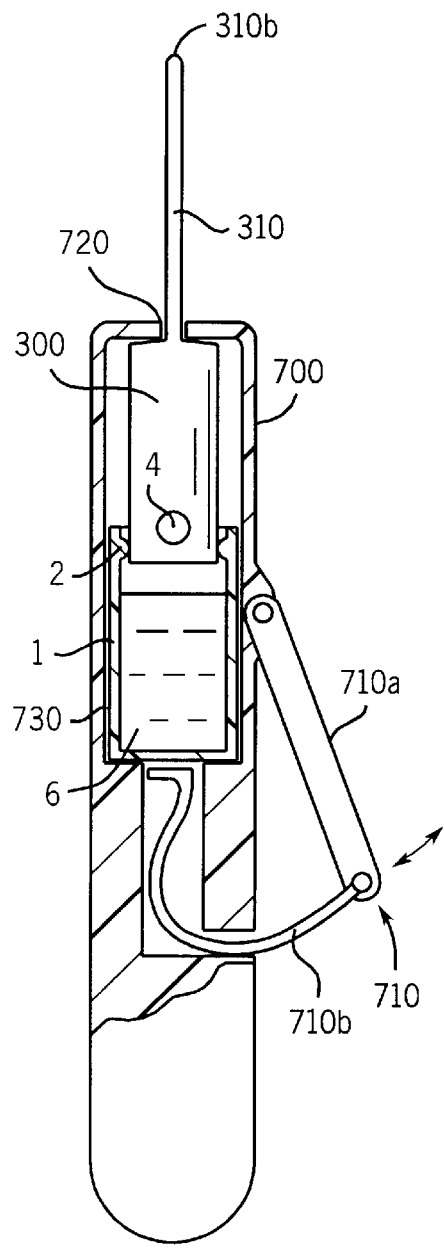
FIG. 15 is a longitudinal sectional view of a another further development of the fourth embodiment of the device of FIG. 10 including a separate manipulating member having a recess for receiving the receptacle and insertion member.

The ampoule device of FIG. 15 substantially corresponds with the device of FIG. 10 and makes use of a separate manipulating member 700 instead of the integrally molded manipulating portion 320. The manipulating member 700 is designed for receiving the receptacle 1 and insertion member 300 in the closed storage position and has retractable slider 710 for manually performing telescoping movement between the receptacle and the insertion member. Member 700 has a pencil like body with a closed lower end and an upper end with a throughgoing hole 720 for inserting the tubular portion 310 of insertion member 300. Furthermore, the pencil like body comprises a side opening in form of a recess 730 for receiving the prefilled device parts 1 and 300 in the closed storage position. The assembled parts 1 and 300 are embedded within the recess 730 after having inserted tubular portion 310 into throughhole 720. The slider 710 of this embodiment consists of lever member 710a pivotally attached to the pencil like body at one end. A metallic blade-spring member 710b is attached to the other free end of lever member 710a with one end. The other free end of spring member 710b, elastically received in member 700, abuts against the bottom of receptacle 1 embedded in the recess 730. Upon pressing down lever member 710a spring member 710b moves receptacle 1 upwards and the substance 6 is forced out through opening 310b. Afterwards, lever member 710a is again retracted to the position shown in FIG. 15 and the empty parts 1 and 300 are removed from recess 730. The member 700 is preferably molded from a rigid plastic material.

Figure 17:
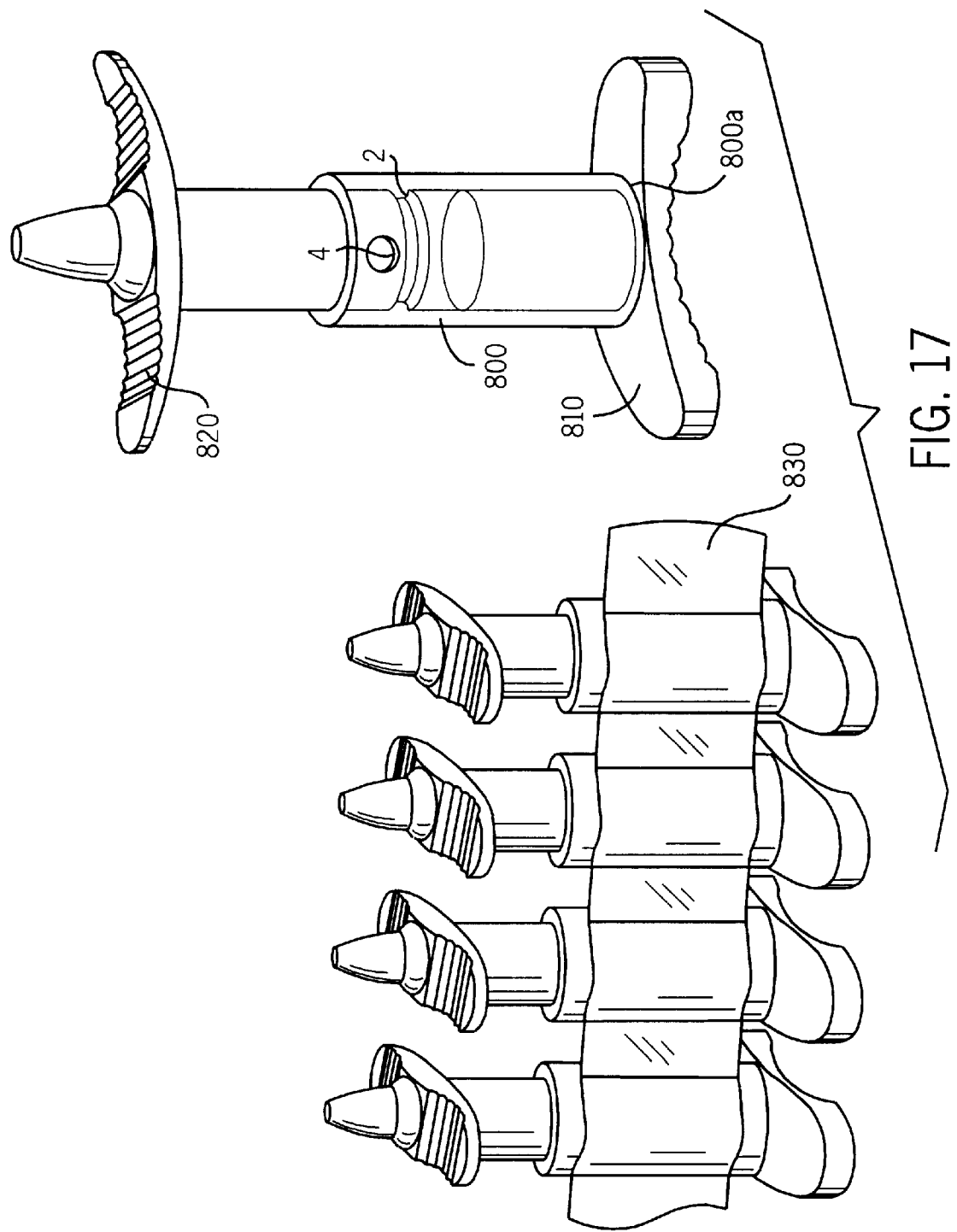
FIG. 17 is a perspective view of a further development of the first embodiment of FIG. 1 and 2 and a perspective view of a plurality of the further developed devices connected together for allowing easier manipulation.

In the embodiment of FIG. 17 the modified receptacle 800 includes a base portion 810 radially extending outwards from the cylindrical body at the closed lower end 800a thereof for manually performing the telescoping movement in cooperation with an integrally molded manipulating means 820 and base portion 810 supporting the ampoule device in an upright position. Manipulating means 820 is similar to manipulating means 320 and comprises a gripping surface. As seen in the left hand part of FIG. 17, a plurality of upright standing ampoule devices are joined together in a line with a strip like fastening means 830. Before using one ampoule device the fastening means 830 is torn apart behind the device or, alternatively, the device body is drawn off from an adhesive strip-like fastening means 830. This allows to subsequently use small amounts of a critical substance (e.g. for eye drop or nose spray appliances).

Figure 18:
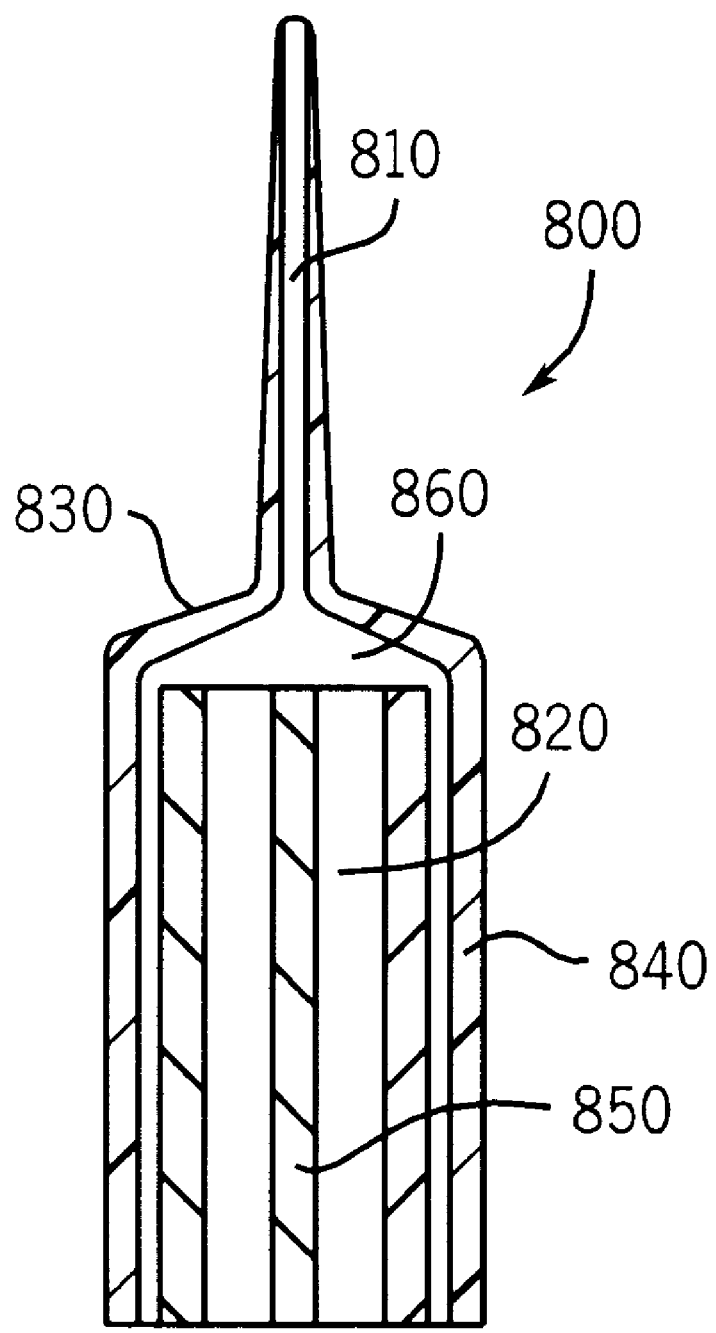
FIG. 18 is a longitudinal sectional view of a modification of the further development shown in FIG. 14.

FIG. 18 shows a modification of the separate manipulating member 500 shown in FIG. 14. The modified manipulating member 800 consists of an outer part 840 and an inner part 850 received in a hollow lower portion of the outer part 840 as seen in FIG. 18. The tubular upper portion of the modified manipulating member 800 encloses the outlet passage 810. The inner part 850 encloses the two axially extending inlet passages 820. The inlet passages 820 are designed for receiving the tubular portion 310 on top of the cylindrical portion of an insertion member 300 and are in fluid communication with the outlet passage 810 via a static mixing zone 860. The manipulating member 800 also includes the shoulder 830 transversely extending outwards with respect to the axially extending outlet passage 810 for manually performing telescoping movement between the two receptacles 1 and insertion members 300 when received in the inlet passages 820 of manipulating member 800. This modified embodiment allows for a better mixing of the substances released from the two insertion members 300 during telescoping movement prior to release from the outlet passage 810 as it allows, due to the two-part construction, a particular design of the static mixing zone 860 above the outlets of the inlet passages 820.

The manipulating members 500 and 800 are molded from a preferably elastomeric plastic material.

A specific implementation of the embodiment shown in FIG. 1 and 2 had the following dimensions in millimeter:

Receptacle 1:
longitudinal length: 19.0
outer diameter: 7.0
inner diameter: 5.5
half-diameter of sealing lip 2: 0.25
Insertion member 3:
longitudinal length: 25.5
outer diameter: 5.4
inner diameter: 4.0
diameter of transverse opening 4: 2.0

A specific implementation of the embodiment shown in FIG. 10 had the following dimensions in millimeter:

Receptacle 1:
longitudinal length: 29.0 outer diameter: 5.8
inner diameter: 4.0
half-diameter of sealing lip 2: 0.2
Insertion member 300:
length of lower cylindrical portion: 29.0
outer diameter of lower cylindrical portion: 3.9
diameter of transverse opening 4: 1.5
diameter of longitudinal passage 50: 0.5
length of upper tubular portion 310: 28.0

What is claimed is:

1. Prefilled telescoping ampoule device comprising:
  a receptacle made of elastomeric material including a hollow cylindrical body having a closed lower end, an open upper end, and a peripheral sealing lip projecting radially inwardly from an inner wall of the cylindrical body between the closed lower end and the open upper end thereof;
  an insertion member including a cylindrical portion having a closed lower end, an open upper end, a transverse opening radially extending from an outer wall into an interior of the cylindrical portion, and a longitudinal passage axially extending within the interior of the cylindrical portion from the transverse opening to the open upper end of the cylindrical portion;
  the cylindrical portion of the insertion member with its closed lower end ahead being inserted into the open upper end of the hollow cylindrical body and being arranged therein for coaxially telescoping movement of the receptacle and the insertion member towards one another from a closed storage position to an open release position;
  wherein, in the closed storage position, the closed lower end of the cylindrical portion of the insertion member is spaced a distance from the lower end of the hollow cylindrical body so as to define therein a cylindrical chamber containing a substance, and the peripheral sealing lip of the cylindrical body is sealingly pressed into circumferential contact with the outer wall of the cylindrical portion of the insertion member at a location above the closed lower end of the cylindrical body and below the transverse opening so as to prevent release of substance from the chamber into the transverse opening and to frictionally hold the insertion member in place within the receptacle during transportation and storage, and wherein in the open release position, after telescoping movement the lower end of the cylindrical portion of the insertion member is positioned at or close to the lower end of the cylindrical body of the receptacle and the transverse opening of the cylindrical portion of the insertion member is located below the sealing lip of the cylindrical body resulting in a reduced volume of the chamber and a release of substance from the chamber into the transverse opening and the longitudinal passage of the cylindrical portion of the insertion member.

2. The ampoule device of claim 1 wherein the hollow cylindrical body of the receptacle has a further peripheral sealing lip projecting radially inwardly from the inner wall of the cylindrical body, which, in the closed storage position, is sealingly pressed into circumferential contact with the outer wall of the cylindrical portion of the insertion member at a location above the transverse opening of the cylindrical portion of the insertion member so as to assist in frictionally holding the insertion member in place within the receptacle during transportation and storage, and which, during telescoping movement from the closed storage position to the open release position, is sealingly pressed into circumferential sliding contact with the outer wall of the cylindrical portion of the insertion member so as to assist in preventing escape of substance from the chamber to the upper open end of the hollow cylindrical body of the receptacle, wherein said further peripheral sealing lip is especially provided if a second substance is contained in the insertion member to prevent escape of the second substance in the closed storage position.

3. The ampoule device of claim 2 wherein the longitudinal passage of the cylindrical portion of the insertion member has in relation to the outer diameter of the cylindrical portion a large inner diameter so as to provide a cylindrical chamber within the cylindrical portion of the insertion member and wherein the ampoule device further comprises a second insertion member including a cylindrical portion having a closed lower end, an open upper end, a transverse opening radially extending from the outside into the interior of the cylindrical portion, and a longitudinal passage axially extending within the interior of the cylindrical portion from the transverse opening to the open upper end of the cylindrical portion;

the cylindrical portion of the second insertion member with its closed lower end ahead being inserted into the open upper end of the cylindrical portion of the first mentioned insertion member and being arranged therein for coaxially telescoping movement of the two insertion members towards one another;

wherein, in the closed storage position, the closed lower end of the cylindrical portion of the second insertion member is located above the transverse opening of the cylindrical portion of the first insertion member so as to define therein a second cylindrical chamber containing a second substance and the inner wall of the cylindrical portion of the first insertion member is sealingly pressed into circumferential contact with the outer wall of the cylindrical portion of the second insertion member so as to prevent release of substance from the second cylindrical chamber within the first insertion member into the transverse opening of the second insertion member and to frictionally hold the second insertion member in place within the first insertion member during transportation and storage, and wherein in the open release position, after telescoping movement, the lower end of the cylindrical portion of the second insertion member is positioned at or close to the lower end of the cylindrical body of the first insertion member and the transverse openings of the cylindrical portions of the two insertion members are radially aligned and located below the sealing lip of the cylindrical body of the receptacle resulting in reduced volumes of the chambers and a release of the two mixed substances from the two chambers into the transverse opening and the longitudinal passage of the cylindrical portion of the insertion member, said longitudinal passage forming a third cylindrical chamber; and wherein not only the receptacle is provided with one sealing lip and a further sealing lip which, in the closed storage position, being respectively located below and above, the transverse opening of the first insertion member, but also the first insertion member is provided with one sealing lip and a further sealing lip which, in the closed storage position, being respectively located below and above the transverse opening of the second insertion member.

4. The ampoule device of claim 3 wherein the cylindrical chambers within the cylindrical portions of the insertion members extend downwardly beyond the respective transverse openings so as to provide additional cup-shaped spaces between the closed lower ends and the transverse openings of the insertion members.

5. The ampoule device of claim 3 wherein the transverse openings extend through the entire transverse length of the cylindrical portions of the insertion members.

6. The ampoule device of claim 3 further including a removable applicator means extending downward into the third cylindrical chamber of the second insertion member.

7. The ampoule device of claim 3 further including a removable closure means closing the upper open end of the third cylindrical chamber of the second insertion member.

8. The ampoule device of claim 7 further including an applicator means attached to the removable closure means and extending downward into the cylindrical chamber of the second insertion member.

9. The ampoule device of claim 3 wherein the third chamber defined within the cylindrical portion of the second insertion member contains a third substance which is mixed within said third chamber with the first substance contained in the first chamber of the cylindrical body of the receptacle and the second substance contained in the second chamber of the cylindrical portion of the first insertion member when the insertion members and the receptacle are telescopingly moved towards one another from the closed storage position to the open release position.

10. The ampoule device of claim 1 wherein the insertion member includes a coaxially extending tubular portion integrally formed on top of the cylindrical portion having a smaller outer diameter than the cylindrical portion and ending on its upper end in an open tip, and the longitudinal passage is provided in form of a narrow conduit extending from the cylindrical body into the tubular portion up to the open tip thereof.

11. The ampoule device of claim 10 wherein the insertion member includes a manipulating means radially extending outwards from the cylindrical portion at a location allowing the telescoping movement of the receptacle-and the insertion member towards one another.

12. The ampoule device of claim 10 further comprising a manipulating member including a tubular front portion enclosing an outlet passage and a rear portion integrally formed therewith and enclosing at least one axially extending inlet passage for receiving the tubular portion on top of the cylindrical portion of an insertion member and being in fluid communication with the outlet passage, and the manipulating member including a shoulder transversely extending outwards with respect to the at least one axially extending inlet passage for manually performing telescoping movement between the receptacle and the insertion member.

13. The ampoule device of claim 12 wherein the rear portion of the manipulating member encloses at least two axially extending inlet passages for receiving the tubular portions on top of the cylindrical portions of two insertion members, both inlet passages being in fluid communication with the outlet passage for mixing the substances released from the two insertion members during telescoping movement prior to release from the outlet passage.

14. The ampoule device of claim 10 further comprising a manipulating member designed for receiving the receptacle and insertion member in the closed storage position and having a retractable slider for manually performing telescoping movement between the receptacle and the insertion member.

15. The ampoule device of claim 1 wherein the receptacle has a longitudinal window axially extending from the open upper end of the cylindrical body downwards to a location which, in the closed storage position, is above the transverse opening of the cylindrical portion of the insertion member, and the insertion member has a projection radially extending outwards from the cylindrical portion through the longitudinal window for sliding movement therein during telescoping movement.

16. The ampoule device of claim 15 wherein the outer part of the projection protruding from the longitudinal window is designed in form of a slider for manual operation.

17. The ampoule device of claim 1 wherein the insertion member includes a release portion formed on top of the cylindrical portion, coaxially extending therewith and having/an open upper end, and the longitudinal passage extends from the cylindrical body into the release portion up to the open upper end thereof.

18. The ampoule device of claim 17 wherein the release portion is tapered towards an open upper tip of reduced diameter and the longitudinal passage extending up to the tip is provided in form of a small diameter conduit.

19. The ampoule device of claim 17 wherein the release portion is designed in form of an essentially cylindrical applicator having an outer diameter larger than the cylindrical portion and the longitudinal passage extends up to the open upper end of the applicator and is provided in form of a small diameter conduit.

20. The ampoule device of claim 19 wherein the open upper end of the applicator has an essentially plane end face which is inclined with respect to the longitudinal axis of the applicator.

21. The ampoule device of claim 17 wherein the release portion is designed in form of a bulgy dropper made of a soft elastomeric material and having an intermediate part of an outer diameter larger than the cylindrical portion and ending in an open droplet tip of reduced outer diameter and the longitudinal passage being in form of a small diameter conduit in the cylindrical portion expands to a larger diameter chamber within the intermediate part of the dropper and reduces to a small diameter outlet in the droplet tip.

22. The ampoule device of claim 1 wherein the transverse opening of the cylindrical portion of the insertion body has an essentially circular cross section and the sealing lip of the cylindrical body of the receptacle has an essentially half-circular cross section of a half-diameter larger than but in the order magnitude of that of the transverse opening.

23. The ampoule device of claim 12 wherein the longitudinal passage has a smaller inner diameter than the transverse opening.

24. The ampoule device of claim 1 wherein the transverse opening is going through an entire transverse length of the cylindrical portion of the insertion member.

25. The ampoule device of claim 1 wherein the longitudinal passage of the cylindrical portion of the insertion member has in relation to an outer diameter of the cylindrical portion a large inner diameter so as to define a cylindrical chamber within the cylindrical portion of the insertion member.

26. The ampoule device of claim 25 wherein the cylindrical chamber within the cylindrical portion of the insertion member extends downwardly beyond the transverse opening so as to provide an additional cup-shaped space between t he closed lower end and the transverse opening.

27. The ampoule device of claim 25 wherein the transverse opening extends through the entire transverse length of the cylindrical portion of the insertion member and has an axially oblong cross-sectional area.

28. The ampoule device of claim 25 further including a removable applicator means extending downward into the cylindrical chamber of the insertion member.

29. The ampoule device of claim 25 further including a removable closure means closeing the upper open end of the cylindrical chamber of the insertion member.

30. The ampoule device of claim 29 further including an applicator means attached to the removable closure means and extending downward into the cylindrical chamber of the insertion member.

31. The ampoule device of claim 25 wherein the cylindrical chamber defined within the cylindrical portion of the insertion member serves as a second chamber containing a second substance which is mixed within the second chamber with the first substance contained in the chamber of the cylindrical body of the receptacle when the insertion member and the receptacle are telescopingly moved towards one another from the closed storage position to the open release position.

32. The ampoule device of claim 25 wherein the receptacle includes a base portion radially extending outwards from the cylindrical body at the closed lower end thereof for manually performing the telescoping movement in cooperation with a manipulating means radially extending outwards from the cylindrical portion of the insertion member, said base portion serving as base for supporting the ampoule device in an upright position.

33. The ampoule device of claim 32 wherein a plurality of said upright standing devices are joined together in a line with a strip like fastening means.

34. The ampoule device of claim 1 wherein a spring means is provided between the closed lower end of the insertion member and the receptacle.

35. The ampoule device of claim 34 wherein said spring means is integrally formed with the lower end of the insertion member.

36. The ampoule device of claim 1 wherein, in said closed storage position, the open upper end of said insertion member and the open upper end of the cylindrical portion of said receptacle are flush.

37. The ampoule device of claim 36 wherein the transverse opening in the outside wall of cylindrical portion of said insertion member substantially extends from the closed lower end to the open upper end of said cylindrical portion and circumferentially extends over substantial portions of said outside wall.

38. The ampoule device of claim 1, wherein the sealing lip of the cylindrical body is sealingly pressed into circumferential contact with the outer wall the cylindrical portion of the insertion member at a location above the transverse opening so as to prevent escape of substance from the chamber to the upper open end of the hollow cylindrical body of the receptacle.

* * * * *